United States Patent [19]

Haak

[11] Patent Number: 5,263,934
[45] Date of Patent: Nov. 23, 1993

[54] STROKE LIMITING SYRINGE WITH RETRACTABLE NEEDLE

[76] Inventor: Abraham van den Haak, Dorpsstraat 14, 9537 TC Eesergroen, Netherlands

[21] Appl. No.: 8,865

[22] Filed: Jan. 25, 1993

Related U.S. Application Data

[63] Continuation of Ser. No. 804,058, Dec. 9, 1991, abandoned.

[30] Foreign Application Priority Data

Nov. 28, 1991 [NL] Netherlands .......................... 9101994

[51] Int. Cl.⁵ .............................................. A61M 5/50
[52] U.S. Cl. ..................................... 604/110; 604/195; 604/198; 604/199; 604/208; 604/220
[58] Field of Search ................ 604/110, 208, 221, 195, 604/220, 190, 199, 240, 243

[56] References Cited

U.S. PATENT DOCUMENTS

| | | | |
|---|---|---|---|
| 2,869,541 | 1/1959 | Helmer et al. ................. | 604/210 |
| 4,642,102 | 2/1987 | Ohmori ............................ | 604/210 |
| 4,790,822 | 12/1988 | Haining ........................... | 604/195 |
| 4,820,272 | 4/1989 | Palmer ............................. | 604/220 |
| 4,883,471 | 11/1989 | Braginetz et al. .............. | 604/220 |
| 5,026,354 | 6/1991 | Kocses ............................. | 604/220 |
| 5,116,319 | 5/1992 | Van Den Haak ................ | 604/110 |
| 5,215,533 | 6/1993 | Robb .............................. | 604/110 |

*Primary Examiner*—John D. Yasko
*Assistant Examiner*—Anthony Gutowski
*Attorney, Agent, or Firm*—Kenyon & Kenyon

[57] ABSTRACT

A syringe having a casing, a shiftable rod assembly, and a needle foot latched at a first end of the casing is disclosed. The syringe is equipped with a shiftable ring for limiting stroke length of the rod assembly in such a way to maintain the piston at a predetermined distance from the needle foot, and to increase the stroke length after a second outward shifting stroke of the piston for drawing in liquid, in such a way that upon a second inward shifting stroke of the piston for expulsion of the injection liquid, the piston will be coupled with the needle foot.

20 Claims, 5 Drawing Sheets

STROKE LIMITING SYRINGE WITH RETRACTABLE NEEDLE

This application is a continuation of application Ser. No. 07/804,058, filed on Dec. 9, 1991 (now abandoned).

BACKGROUND OF THE INVENTION

The invention relates generally to syringes and more particularly to an improved syringe having a piston/piston rod assembly that is shiftable within a casing.

Such a syringe is disclosed in Netherlands patent application 90 00 487. Syringes of this type typically draw in liquid from a storage bottle that is sealed by a pierceable stopper. The piston/piston rod assembly is packaged in the extended condition. The air present in the syringe is driven into the bottle when the needle is inserted into the bottle, so that, upon subsequent withdrawal of the needle, the drawing in of liquid is not impaired by the lower pressure in the bottle. Prior to injection of the liquid into the patient, the remaining air in the syringe is ejected by directing the needle upwards. As the piston is completely pressed inwards during injection, coupling with the needle foot takes place.

A syringe thus made has the advantage that the air in the prepacked syringe may be made sufficiently sterile to avoid contamination of the contents of the bottle. A disadvantage is that the prepacked syringe has a considerable length, so that such prepacked syringes take up much space. Another disadvantage occurs in the event of incorrect operation of this syringe, whereby the coupling of the piston with the needle foot can take place prematurely. A further disadvantage is that the stroke limiting means have a relatively complicated shape, which increases manufacturing cost. Since such syringes are meant to be disposable, costs must be limited as much as possible.

SUMMARY OF THE INVENTION

The invention provides a syringe that can be prepacked in its inwardly shifted position and that can be manufactured very cheaply.

The present invention relates to an improved syringe with a built-in two-stroke mechanism that restricts the first inward stroke length of the piston rod so that the coupling end of the piston rod remains at a small distance from the needle foot. Only after the piston rod is pressed inward a second time, upon injection of the liquid into the body, can the piston rod be pushed inward sufficiently for coupling of the piston head and the needle foot.

The increase of the stroke of the assembly takes place after the assembly has been pressed inwards for the first time following the drawing in of air, so that coupling with the needle foot can take place only after the assembly is pressed inwards for the second time.

DETAILED DESCRIPTION

Figure 1:
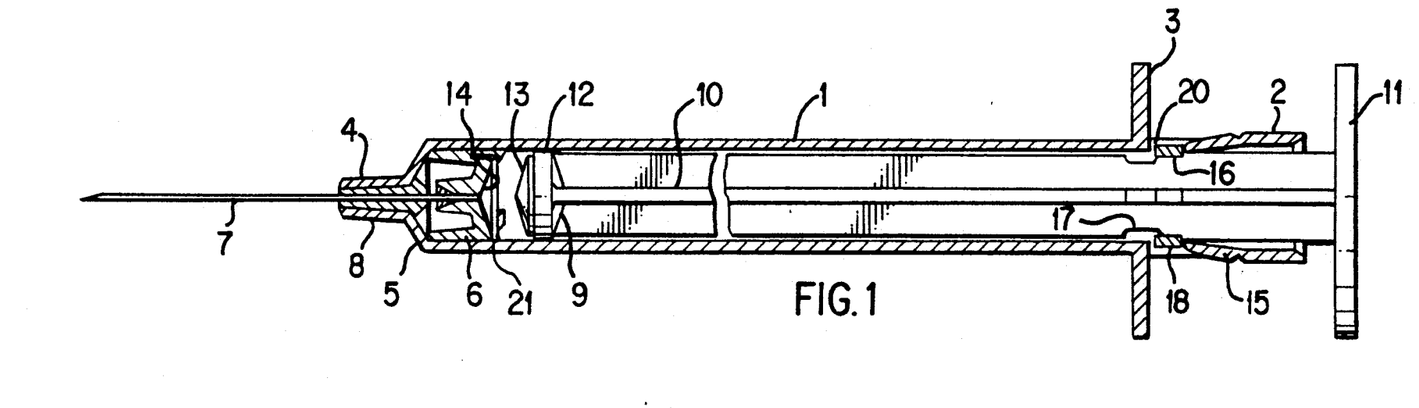
FIG. 1 is a diagrammatical section of a first embodiment of the syringe according to the invention.

FIG. 1 shows a first embodiment of the syringe according to the invention. This comprises a generally cylindrical casing 1, having, at some distance from the open end 2, a gripping ring 3, and at its other end, a narrowed nose 4 which adjoins the casing 1 via a generally conical surface 5.

From the open end 2 a needle foot 6 is pushed into the casing 1, to which a hollow needle 7 is attached, the needle shiftably projecting outwards through a bushing 8 placed in the gradually narrowing nose 4. The needle foot 6 abuts the conical connecting surface 5 and is prevented from shifting in a way to be described hereinafter to ensure that in case of a longitudinal force being exerted on the needle 7, for instance in case of the piercing of the stopper of a storage bottle of injection liquid or the skin of a patient, the needle foot cannot be pressed inwards.

In assembling such a syringe all parts may be consecutively inserted into the casing 1 from the open end 2. More particularly, the needle 7 may be inserted through the bushing 8 and then fixed in the needle foot 6 (for instance with an adhesive), after which the needle foot 6 may be inserted into the casing 1 with the needle 7 and the bushing 8. During its passage through the nose 4, the needle 7 is suitably guided in an axial direction so that damage to the needle is avoided (see also FIGS. 3B and 3C to be described hereinafter).

Such a syringe may also be adapted to use separate needles fitted from the outside, as described in the abovementioned prior patent application 90 00 487.

An assembly of a piston 9 and a piston rod 10 connected therewith is also inserted into the casing 1, the piston rod 10 having at its free end a pressing surface 11 with which the piston rod 10 can be operated. The piston 9 has a sealing ring 12 which provides a liquid-tight seal against the inner wall of the casing 1, and is further provided with a conical surface 13 at the side directed towards the needle foot 6. The needle foot 6 has a corresponding conical surface 14, such that when the piston rod 10 is completely pressed in, the dead space between the needle foot 6 and the piston 9 becomes as small as possible.

Furthermore, means, to be described hereinafter, are present to provide coupling between the piston 9 and the needle foot 6 when the piston 9 is completely pressed in and to simultaneously unlock the needle foot 6, in such a way that after providing said coupling and unlocking, the needle foot 6 can be drawn inwards into the casing 1 along with the needle 7.

Figure 2A:
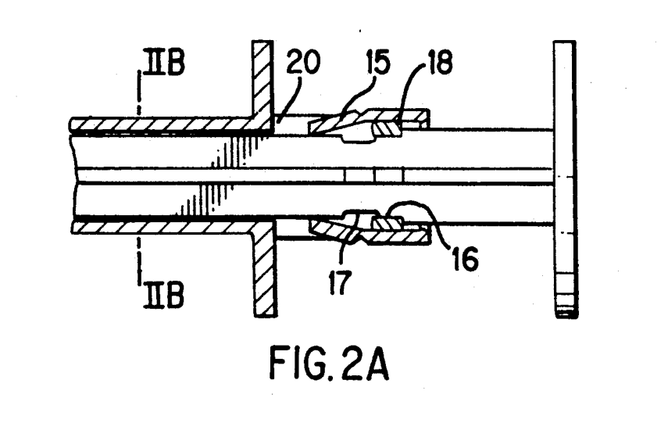
FIGS. 2A, 2B and 2C are partial diagrammatical sections of the first embodiment of the syringe.
Figure 2B:
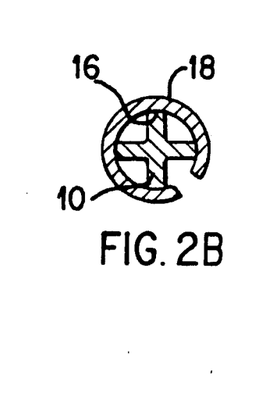
Figure 2C:
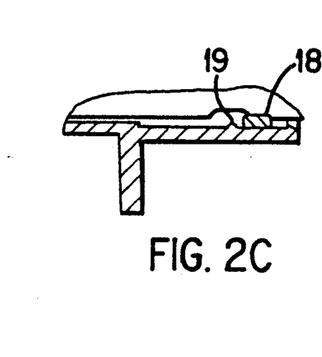

Near the open end 2 of the casing 1, the casing is provided with a number of inwardly..resilient tongues 15, as may be seen more clearly in FIG. 2A. On the piston rod 10 there are formed two portions with a smaller diameter, which form two support surfaces 16 and 17, the surface 17 with the smaller diameter being located away from the pressing surface 11. In FIG. 2B, the piston rod 10 is in the form of a cruciform, and support surfaces 16 and 17 are situated in the ribs thereof. On the support surface 16, there is, in the initial situation, an inwardly resilient ring 18, i.e., a split ring or a coil spring, that rests on the support surface 16 with an inward tension. As shown in FIG. 2C, a small lug 19 may be provided near the inward end of the support surface 16 on the inner wall of the casing 1 to retain the ring 18 against accidental shifting on this support surface 16.

FIG. 2A shows the initial situation. When air is drawn in and then driven out into a storage bottle, the piston rod cannot be pressed further inwards than the position shown in FIG. 1, the ring 18 then abutting an abutment shoulder 20, as in this situation the external diameter of the ring 18 is greater than the internal diameter of the casing 1 at this shoulder 20. The stroke length of the piston 9 is thereby limited to such an extent that it cannot unlatch and be coupled with the needle foot 6. The tongues 15 now grip behind this ring, as shown in FIG. 1.

When the piston rod 10 is withdrawn again, in order to draw in injection liquid, the tongues 15 retain the ring 18, shifting it to the support surface 17, the diameter of the ring decreasing as a result of its inward resilience. This causes the ring 18 to be liberated from the ends of the tongues 15, so that the piston rod can be drawn out unimpeded, the external diameter of the ring having now also become smaller than the internal diameter of the casing 1. In the course of subsequent pressing inwards of the piston rod 10 for the expulsion of injection liquid, the piston 9 can then be pressed through to the needle foot 6, in the course of which practically all the injection liquid can be expelled as a result of the conical form of the surfaces 13 and 14, which is advantageous especially in the case of expensive injection fluids.

As soon as the piston 9 reaches the needle foot 6, the latter is unlatched and coupling between the two is brought about, so that when the piston rod 10 is pulled outwards, the needle foot is drawn along and the needle 7 comes to lie inside the casing 1. The complete device can then be disposed of as such. It is also possible to destroy the needle by pressing in the piston rod 10 once more, the point of the needle, which is somewhat curved or somewhat eccentrically guided, abutting the end surface of the bushing 8 or the conical surface 5, and the needle is bent beyond use. In addition, the passage in the bushing 8 is so narrow that the chance of the needle reentering this passage is extremely small.

Figure 3A:
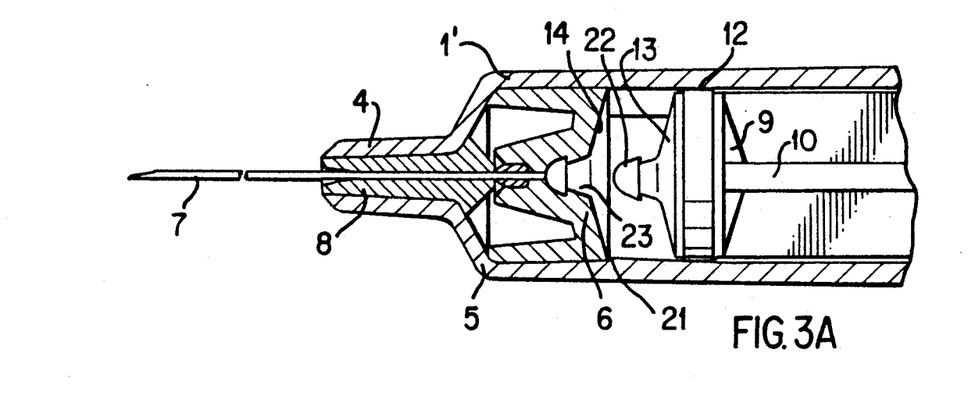
FIGS. 3A, 3B, 3C and 3D are partial diagrammatical sections of the terminal portion of a syringe illustrating the latching and coupling means of the needle foot and the piston.
Figure 3B:
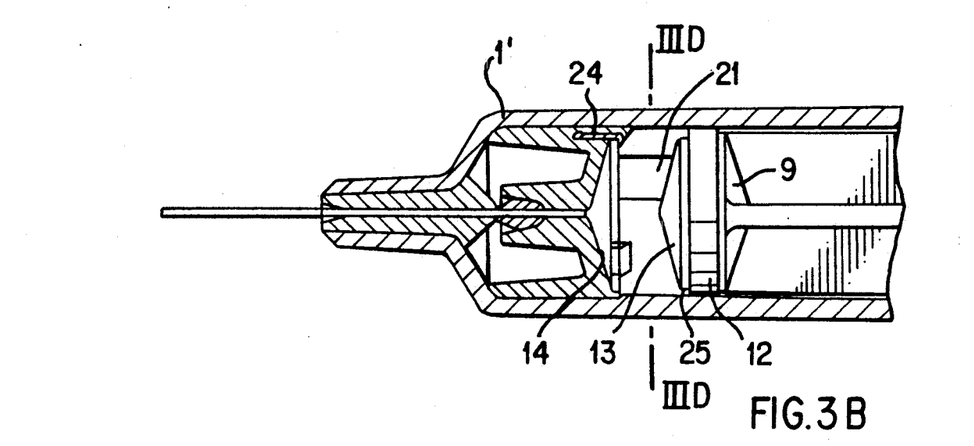
Figure 3C:
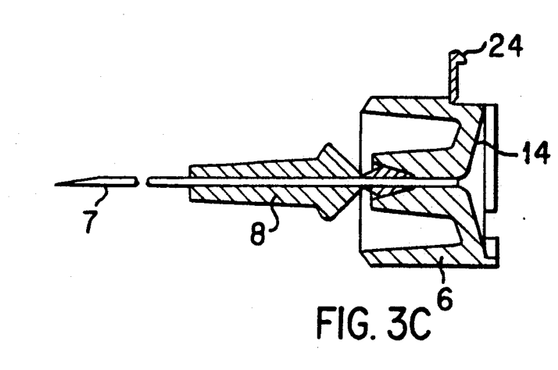

The means for latching the needle foot 6 in the casing 1 and for coupling the piston 9 to the needle foot 6 may be provided in different ways. FIGS. 3A-C show examples of embodiments thereof.

As shown in FIG. 3A, the end portion 1' of the casing 1 is provided with internal shoulders 21 which are distributed along the circumference at an angle of, for instance, 120°, the end portion 1' of the casing 1 being slightly narrowed and elastically deformable. The needle foot 6 is slid in from the open end 2 during assembly of the syringe, the end portion 1' and possibly also the needle foot 6 being deformed somewhat until the needle foot 6 snaps behind the shoulders 21. Upon complete pressing inwards of the piston 9, the latter deforms the end portion 1' somewhat, the shoulders 21 being moved back, while simultaneously a knob 22 on the surface of the piston head forcing its way into a correspondingly shaped recess 23 in the needle foot 6 and bringing about a coupling therewith. The needle foot 6 can then be withdrawn past the shoulders 21.

FIGS. 3B and 3C show a somewhat modified embodiment of the needle foot 6 and the piston 9, the head 13 of the piston being shaped as a smooth cone as in the case of FIG. 1, and the needle foot 6 being provided with a correspondingly conical surface 14. The needle foot 6 has one or more somewhat projecting hooks 24 which, as shown in FIG. 3C, can protrude outwards in a transverse direction when free in order to facilitate the forming thereof in a single operation. In the course of sliding the needle foot 6 into the casing 1, these hooks 24 bend inwards, so that they lie flat against the inner wall of the casing 1. Upon complete pressing inwards of the piston 9, the ends of these hooks 24 engage a groove 25 between the piston head 13 and its sealing ring 12 so that coupling can be brought about in a simple way. There may, for instance, be three hooks 24 present, which must then be situated in the interspaces between the lugs 21, as shown, the piston rod in this case having three ribs.

FIG. 3C further shows that before introducing the needle foot 6, the bushing 8 is placed onto the needle 7 to guide the needle during passage through the wider nose 4, as described hereinabove.

Figure 3D:
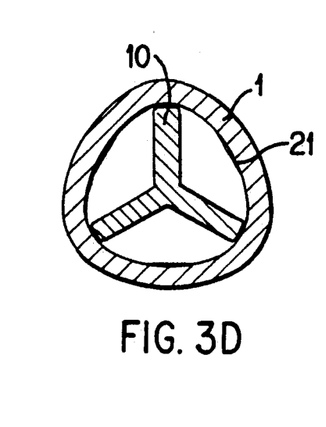

More particularly, as shown in FIG. 3D, the casing 1, the needle foot 6, and the piston 9 are made with a somewhat triangular cross-section, the piston rod 10 being made with three ribs. The piston 9 and the needle foot 6 are then guided non-rotatably in the casing 1. The lugs 21 are situated on the sides of the triangular casing wall, whereas the hooks 24 of the needle foot are situated opposite the corners. Upon complete pressing inwards of the piston 9, the lugs 21 are pushing away by the bevelled piston head 13, by which action the needle foot 6 is freed, so that after engaging of the hooks 24 with the piston 9, the needle foot 6 can be drawn inwards together with the piston 9.

The advantage of this is that the position of the hooks 24 relative to the lugs 21 is unambiguously fixed. An additional advantage is that a syringe thus made cannot roll about, and due to the flattened surfaces the casing 1 can be brought closer to the skin during injection. It will be obvious that these advantages may also be achieved using other non-circular cross-sections. All this is made possible by the fact that all parts may be formed by injection moulding or similar methods out of plastic material.

In the case of the embodiment according to FIGS. 1 and 2, it is possible that after removing a syringe from its packaging, the piston rod is accidentally pressed into the position shown in FIG. 1, so that after withdrawal of the piston for drawing in air, the ring 18 slides onto the support surface 17, thus removing the stroke limitation. To prevent this, the embodiment according to FIG. 4 may be used, in which another surface 26 with an even greater diameter, on which the ring 18 rests in the initial situation, adjoins the support surface 16. Casing 1 is provided on its inner wall an abutment surface 27, the ring 18 in the initial situation resting against the abutment surface 27 so that pressing inwards of the piston rod 10 is thereby prevented. Upon drawing outwards of the piston rod, the ring 18 is retained by one or more abutment surfaces 28 on the other side of the ring 18, so that the ring 18 is pressed onto the first support surface 16, the diameter of the ring decreasing to such an extent that it can slide away under the abutment 27 when the piston rod 10 is pressed back in for the expulsion of air, after which the operation continues as described with reference to FIGS. 1 and 2. The abutments 28 may for instance be circumferentially staggered in relation to the tongues 15. In the initial position, the ring 18 is then locked between the abutments 27 and 28 and is freed from both abutments during shifting towards the surface 16.

Figure 4:
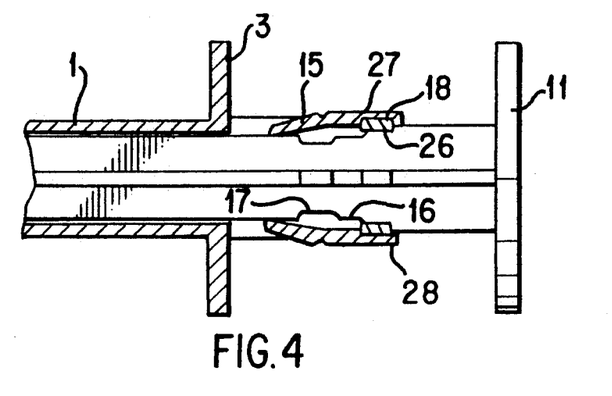
FIG. 4 is a diagrammatical section of the terminal portion of a modified embodiment of the syringe according to FIGS. 1 and 2.

In the embodiments according to FIGS. 1, 2 and 4 with an inwardly resilient ring it is possible that during protracted storage the ring 18 loses some of its resilience, so that, upon being shifted, its external diameter does not decrease sufficiently for the ring to fit closely on the support surface 17, so that, eventually, the piston rod 10 cannot be pressed inwards sufficiently.

Figure 5:
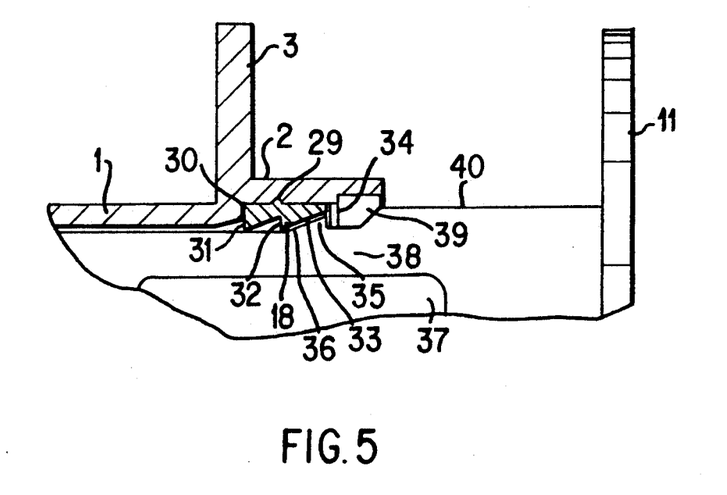
FIG. 5 is a corresponding diagrammatical section of a second embodiment of the syringe according to the invention.

FIG. 5 shows a preferred embodiment in which this drawback does not exist. The ring 18 is now seated in a widened seat 29 with a transverse shoulder 30 in the end portion 2, the end surface 31 of the ring 18 resting against this shoulder 30. The ring 18 has an internal shoulder 32 adjoined by an diverging sloping surface 33, which ends in a somewhat sloping end surface 34.

The piston rod 10 shown in the initial position has a draw hook 35 adjoined by a sloping surface 36 which is generally parallel to the diverging sloping surface 33 of the ring 18. The underlying portion of the piston rod has a central aperture 37 which makes the intermediate piston rod portion 38 somewhat inwardly resilient. On the outside of the hook 35 there is a somewhat sloping shoulder 39 which is generally parallel with the end surface 34 of the ring 18.

When, during expulsion of air after the piston rod 10 is initially drawn out, sloping surface 36 of the draw hook 35 slides over sloping surface 33 of the ring, with elastic deformation of the intermediate portion 38 of the piston rod 10, until the draw hook 35 snaps behind the internal shoulder 32 of the ring. The sloping shoulder 39 of the piston rod 10 prevents further pressing inwards of the piston rod 10 and coupling of the piston 9 with the needle foot 6 by abutting the end surface 34.

When the piston rod 10 is drawn back out to draw in injection liquid, the hook 35 takes with it the ring 18 which, after leaving the widened seat 29 of the end portion 2, will expand outwards, this being enhanced by the further expansion of the briefly compressed piston rod portion 38. When subsequently the piston rod 10 is pressed inwards once more to expel the liquid the, end surface 31 of the ring 18 abuts the head surface 30 of the end portion 2. The ring 18 is shifted with its sloping surface 33 past the sloping shoulder 39 of the piston rod 10 towards a wider end portion 40 of the piston rod 10 and is further widened. The stroke limitation is thus removed, so that coupling between the piston 9 and the needle foot 6 can take place.

It is possible that the piston rod 10 is accidentally pressed inwards from the initial position, and that the draw hook 35 of the piston rod 10 is then engaged with the recessed shoulder 32 of the ring 18.

Figure 6A:
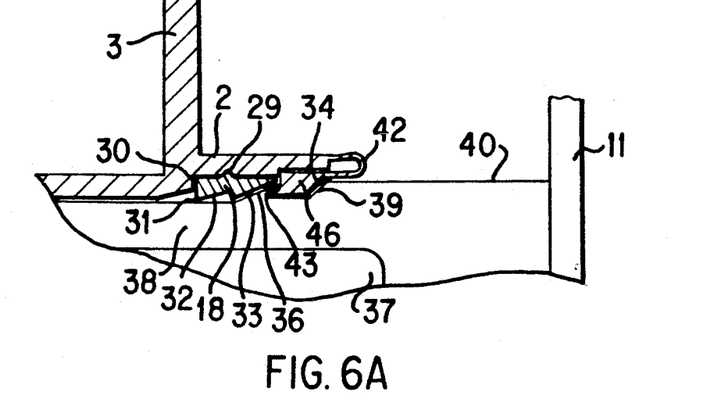
FIGS. 6A, 6B and 6C are partial diagrammatical sections of a modified embodiment of the syringe according to FIG. 5.

FIG. 6A shows a somewhat modified embodiment, there being provided within the widened seat 29 of the end portion 2 of the casing between the draw hook 35 and the sloping shoulder 39, a filler piece 46 which may be connected to the casing 1 by a flexible strip 42. The filler piece 46 prevents pressing inwards of the piston rod 10, but, when the piston rod 10 is drawn outwards for the first time, the filler piece 46 is drawn outwards by the draw hook 35, because a transverse surface 43 of the filler piece 46 engages the draw hook 35 of the piston rod 10, after which the filler piece can fall away or stay attached to the strip 42. Instead of a filler piece a divided ring may be used, which, like the ring 18, can be slid on over the piston rod end.

Figure 6B:
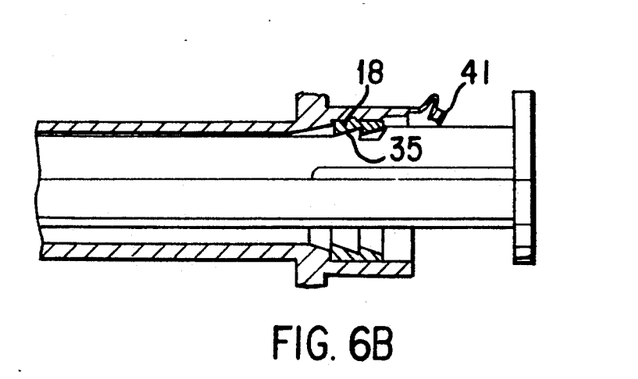
Figure 6C:
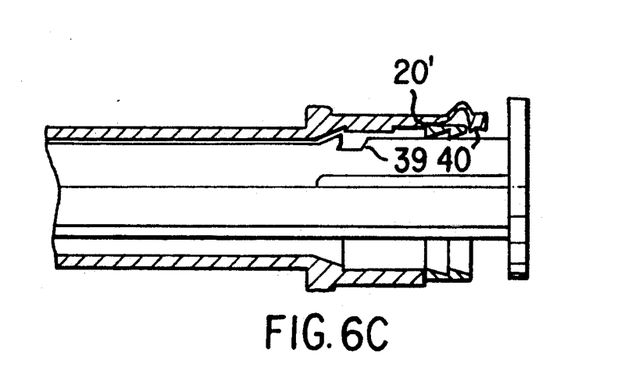

FIGS. 6B and 6C show two extreme inward end positions of the piston rod after the expulsion of air and liquid, respectively, the filler piece 41 being already removed, so that these positions apply equally to the embodiment according to FIG. 5. In the position of FIG. 6B, the transverse shoulder 30 in the end portion 2 of the casing abuts the ring 18 which is still situated in widened seat 29 in the end portion 2 which limits the inward stroke length, while in FIG. 6C the ring 18 is shifted onto the piston rod portion 40 and is retained by the end surface 20' of the casing end 2, the stroke length no longer being limited.

Figures 7A, 7B, 7C:
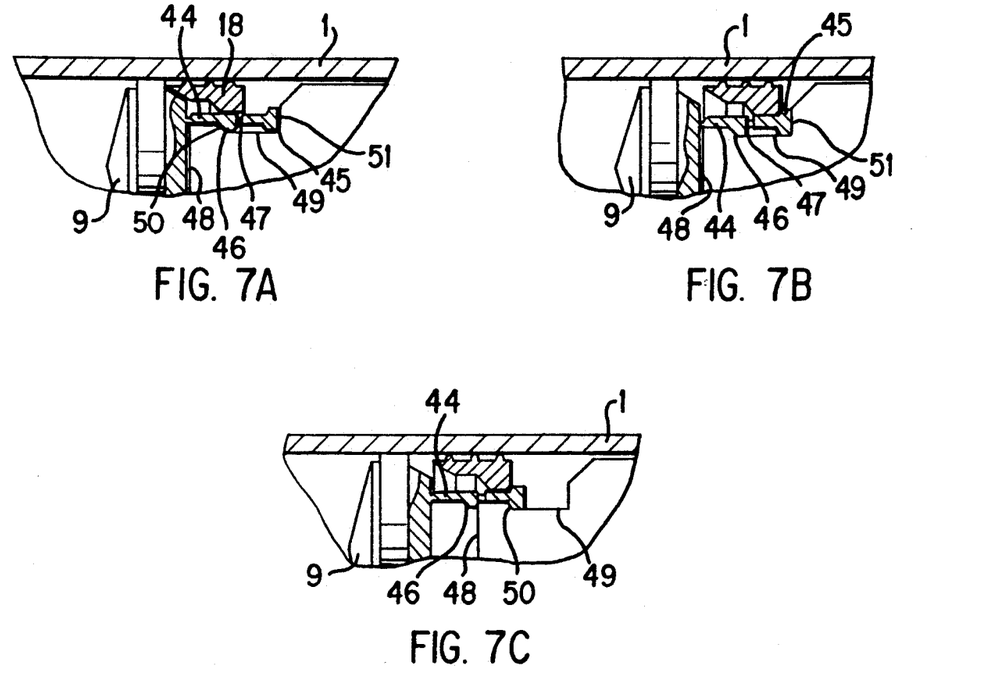
FIGS. 7A, 7B and 7C are partial diagrammatical sections of a third embodiment of the syringe according to the invention.

FIG. 7 shows yet another embodiment, the stroke limiting means being situated near the piston 9. The piston further has two pairs of hooks 44 and 45, the hooks 44 at least being outwardly resilient. The hooks 44 each have at their piston sides a sloping surface 46, and on the other side a straight head surface 47. The piston rod 10 has a head surface 48, which, in the initial position illustrated in FIG. 7A, rests against the rear surface of the piston 9, while a narrowed portion 49 is provided with a bevel 50, which engages the sloping surface 46 of the hook 44. At a certain distance of the bevel 50, the narrowed portion 49 adjoins a transverse surface 51, which in the initial position is close to or against the end surface of the second hook 45. In this initial position a ring 18 rests on the external surface of the hooks 44, the ring 18 further fitting with friction against the internal wall of the casing 1. The hooks 44 are then locked against bending outwards, so that the piston rod is fixedly coupled to the piston 9 for pressing as well as drawing forces.

When air is drawn in, the ring 18 is carried along by the piston 9. However, as soon as the piston rod 10 is pressed back in for the expulsion of air, the ring 18 will be held back by friction with the casing 1 and, as shown in FIG. 7B, will be shifted towards the hooks 45. The pressing forces are still transferred to the piston 9 by the head surfaces 48 and/or 51 of the piston rod 10.

When, as shown in FIG. 7C, liquid is drawn in and a pulling force is exerted on the piston rod 10, the bevelled surface 50 of the narrowed portion 49 of the piston rod 10 slides over the corresponding sloping surfaces 46 of the hooks 44, these hooks then being allowed to bend outwards, after which the head portion 48 of the piston rod 10 comes to lie between the hooks 44 and 45, the hooks 45 being locked against outward movement by the ring 18.

As shown in FIG. 7C, the actual length of the piston rod is now increased by the length of the hooks 44, so that upon subsequent pressing inwards of the piston rod for the expulsion of liquid, the piston rod 10 can be pressed inwards over a correspondingly greater distance, this distance being sufficient to bring about coupling with the needle foot.

Additional abutments (not shown) on the piston rod 10 and the casing 1 may limit the inward shifting of the piston rod to a distance at which, in the position shown in FIG. 7, coupling between the piston 9 and the needle foot 6 cannot take place. In this situation, the syringe can readily be packaged.

Figure 8A:
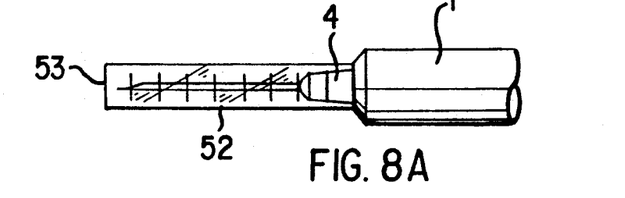
FIGS. 8A and 8B are diagrammatical representations of a needle cap for such a syringe.
Figure 8B:
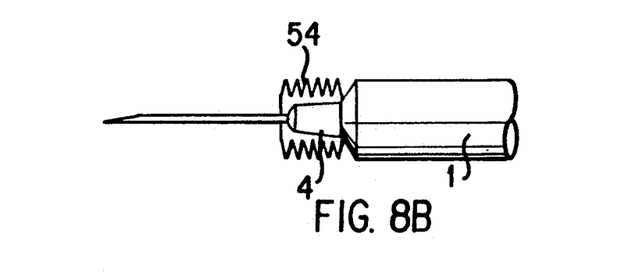

Although a syringe according to FIGS. 1 through 7 may be packaged in a generally sterile condition, it is necessary for drawing in liquid from a liquid bottle to first fill the syringe internally with air. If this is ambient air, there is a risk that this air, which is pressed into the storage bottle, may contaminate its contents and that of the syringe. In order to prevent this, a cap 52 may be provided on the needle 7, as shown in FIG. 8A, which is loosely fitted onto the end 4 of the casing 1 and is provided with a filter 53 adapted to block out dust from the air. To insert the needle into a liquid container the cap must be removed. It is also possible, as shown in FIG. 8B, to provide this cap with a collapsible wall 54, it being possible then to insert the needle 7 through the end thereof before sticking the needle through the stopper of a liquid container. The cap 52 is then folded like an accordion, and can then be left around the needle 7.

I claim:

1. A syringe comprising
   a casing having a first needle end and an open end;
   a piston/piston rod assembly shiftable in said casing, said assembly having a first stroke length corresponding to a distance between a first outward shifting stroke of the assembly for drawing in air and a first inward shifting stroke of the assembly for the expulsion of air, said assembly having a second stroke length corresponding to a distance between a second outward shifting stroke of the assembly for drawing in injection liquid and a second inward shifting stroke of the assembly for the expulsion of liquid;
   a needle foot latched at said first end of the casing;
   a needle coupled to the needle foot;
   means for coupling the piston and the needle foot to unlatch and inwardly draw the needle foot and needle into the casing, with the piston, to shield off the needle from the exterior of the casing; and
   a stroke limiting means for limiting the first stroke length of the assembly during the first inward shifting stroke of the piston to maintain the piston at a predetermined distance from the needle foot, and to increase the second stroke length such that the piston engages the needle foot;
   wherein the stroke limiting means further comprises a ring, shiftable relative to and enagageable with either the assembly or the casing; whereas the ring, in an initial position, limits the first stroke length of the assembly by cooperation with either the casing or the assembly, and is shifted from the initial position to a shifted position by cooperation with either the casing or the assembly, thereby removing said limitation on the stroke length and allowing for said increased second stroke length of the assembly; said syringe further comprising
   a transverse abutment shoulder provided on the casing, said shoulder having a diameter such that the ring, in the initial position, but not in the shifted position, engages the shoulder to limit the first stroke length of the assembly; and
   first and second support surfaces provided on the piston rod, wherein the second support surface is situated towards the piston and the first support surface is situated in an axial direction opposite to the second support surface, said second support surface having a diameter smaller than a diameter of the first surface;
   wherein the ring is an inwardly resilient ring, which in the initial position rests against the first support surface and has a first external dimension, and in the shifted position rests against the second support surface and has a second external dimension smaller than the first external dimension.

2. The syringe according to claim 1, further comprising
   at least one inwardly resilient tongue provided on the casing;
   wherein the inwardly resilient tongue, in an initial position, is situated between the ring and the shoulder, and shifts the ring towards the second support surface upon the second outward shifting stroke of the assembly, thereby releasing the ring from the tongues and the shoulder to increase the second stroke length of the assembly.

3. The syringe according to claim 2, further comprising one or more protruding ribs or lugs provided on the inner wall of the casing to prevent the accidental shifting of the ring towards the second support surface.

4. The syringe according to claim 2, further comprising
   a third support surface, wherein the first support surface adjoins, at the side opposite the second support surface, the third support surface; the third support surface having a greater diameter than the first surface; one or more abutments on the inner wall of the casing or tongues;
   whereas the ring prior to the initial position is situated on the third support surface and abuts said one or more abutments situated on the inner wall of the casing or of the tongues, on the side of the ring towards the first support surface, to prevent the assembly from being shifted inward in a stored condition; and the ring, upon a first outward shifting stroke of the assembly, is transferred to the first support surface by cooperation with one or more additional abutments on the inner wall of the casing or of the tongues, on the other side of the ring.

5. A syringe according to claim 1, further comprising means for destroying the needle upon a third inward shifting stroke of the piston assembly subsequent to being drawn inward into the casing.

6. The syringe according to claim 1, wherein the ring is a split ring.

7. The syringe according to claim 1, wherein the casing is provided at its needle end with a nose in which a bushing, having a guide bore for the needle, fits.

8. The syringe according to claim 1, wherein the needle foot is restrained against inward shifting by one or more abutment edges of the casing, and the casing wall and the piston is deformable in such a way that, upon the second inward shifting stoke of the piston along the increased stroke length, the piston couples with the needle foot, permitting the needle foot to be withdrawn past the abutment edges.

9. The syringe according to claim 8, wherein the needle foot is provided with one or more protruding hooks that are adapted to grip elastically behind an edge of the piston to couple the piston with the needle foot after the stroke length of the piston has been increased.

10. The syringe according to claim 9, wherein, the casing, the needle foot and the piston each have a non-circular section, and the hooks of the needle foot are situated at the portions thereof with the greatest radius.

11. The syringe according to claim 1, wherein the piston and the needle foot are provided with conical surfaces of at least approximately the same shape, which upon complete pressing inward of the piston, at least approximately interfit.

12. The syringe according to claim 8, wherein the casing is provided, at its needle end, with an inwardly directed support surface, against which the needle foot rests, to lock the needle foot between the support surface and the abutment edges.

13. The syringe according to claim 1, wherein a needle cap is provided on the outside of the casing, to surround the needle, and is adapted to allow sterile air to be drawn into the casing upon a first outward shifting stroke of the assembly.

14. The syringe according to claim 13, wherein the needle cap is provided with a suction filter.

15. The syringe according to claim 13, wherein the wall of the needle cap is collapsible upon insertion of the needle into a container.

16. The syringe according to claim 13, wherein the needle cap is accordion-shaped, and at its closed end may be penetrated by the point of the needle to allow the cap to be rearwardly compressed so as to uncover the needle.

17. A syringe comprising
a casing having a first needle end and an open end portion;
a piston/piston rod assembly shiftable in said casing, said assembly having a first stroke length corresponding to a distance between a first outward shifting stroke of the assembly for drawing in air and a first inward shifting stroke of the assembly for the expulsion of air, said assembly having a second stroke length corresponding to a distance between a second outward shifting stroke of the assembly for drawing in injection liquid and a second inward shifting stroke of the assembly for the expulsion of liquid;
a needle foot latched at said first end of the casing;
a needle coupled to the needle foot;
means for coupling the piston and the needle foot to unlatch and inwardly draw the needle foot and needle into the casing, with the piston, to shield off the needle from the exterior of the casing; and
a stroke limiting means for limiting the first stroke length of the assembly during the first inward shifting stroke of the piston to maintain the piston at a predetermined distance from the needle foot, and to increase the second stroke length such that the piston engages the needle foot;
wherein the stroke limiting means further comprises a ring, shiftable relative to and engageable with either the assembly or the casing; whereas the ring, in an initial position, limits the first stroke length of the assembly by cooperation with either the casing or the assembly, and is shifted from the initial position to a shifted position by cooperation with either the casing or the assembly, thereby removing said limitation on the stroke length and allowing for said increased second stroke length of the assembly;
said ring being an outwardly expandable ring that is shiftable in a widened seat in the end portion of the casing and is restrained therein against inward shifting; the ring having an inner side that is provided with a recessed shoulder that adjoins a diverging sloping surface directed towards the end portion of the casing and opening outwards, terminating in an outward end surface; and
the piston rod further comprises a draw hook which, in the initial position, is situated against the diverging sloping surface of the ring, and is slidable over the sloping surface of the ring upon the first inward shifting stroke of the assembly to finally grip behind the recessed shoulder of the ring; and a sloping shoulder that abuts the end surface of the ring to limit the first inward stroke length of the assembly; and
whereas the ring is drawn out of the widened seat in the end portion of the casing upon the second outward shifting stroke of the assembly and is allowed to expand, and upon the second inward shifting stroke of the assembly for the expulsion of liquid, the ring in the expanded condition abuts a head surface of the widened seat of the casing, causing the ring with its sloping inner surface to be shifted along past the sloping shoulder of the piston rod, thereby allowing the increase of the second stroke length of the assembly.

18. The syringe according to claim 17, wherein the piston rod portion within the draw hook is inwardly resilient.

19. The syringe according to claim 17, further comprising a filler piece provided inside the widened seat in the end portion of the casing which at least approximately fills up the intermediate space between the draw hook and the sloping shoulder of the piston rod, such that inward shifting of the assembly is prevented in a stored condition, and upon a first outward shifting stroke of the assembly the filler piece is withdrawn from the casing and is liberated therefrom.

20. A syringe comprising
a casing having a first needle end and an open end;
a piston/piston rod assembly shiftable in said casing, said assembly having a first stroke length corresponding to a distance between a first outward shifting stroke of the assembly for drawing in air and a first inward shifting stroke of the assembly for the expulsion of air, said assembly having a second stroke length corresponding to a distance between a second outward shifting stroke of the assembly for drawing an injection liquid and a second inward shifting stroke of the assembly for the expulsion of liquid;
a needle foot latched at said first end of the casing;
a needle coupled to the needle foot;
means for coupling the piston and the needle foot to unlatch and inwardly draw the needle foot and needle into the casing, with the piston, to shield off the needle from the exterior of the casing; and
a stroke limiting means for limiting the first stroke length of the assembly during the first inward shifting stroke of the piston to maintain the piston at a predetermined distance from the needle foot, and to increase the second stroke length such that the piston engages the needle foot;
wherein the stroke limiting means further comprises a ring, shiftable relative to and engageable with either the assembly or the casing; whereas the ring, in an initial position, limits the first stroke length of the assembly by cooperation with either the casing or the assembly, and is shifted from the initial position to a shifted position by cooperation with either the casing or the assembly, thereby removing said limitation on the stroke length and allowing for said increased second stroke length assembly; wherein the stroke limiting means further comprises
two pairs of outwardly resilient locking lugs provided on the piston; the first locking lug of the pairs being axially positioned on the piston; the second locking lug of the pairs being axially positioned on the side of the first locking lug away from the piston; said locking lugs being bevelled on the side away from the piston; the axial length of the first locking lug of the pairs corresponding to the predetermined distance from the needle foot; the inner side of the ring being shiftable around the outside of the locking lugs, while the outer side of the ring fits with friction inside the casing; the width of the inner surface of the ring that contacts the locking lugs being no greater than the axial length of a locking lug so that the locking lug engaged by the ring is locked by the ring;

a shoulder disposed on the piston rod; and whereas the ring engages the first locking lug in the initial position so that the piston rod is fixedly coupled to the piston, then upon the first inward shifting stroke, engages the second locking lug to permit, upon the second outward shifting stroke of the assembly, the shoulder on the piston rod to slide over the bevelled edge of the first outwardly resilient locking lug and engage the second locking lug, thereby increasing the second stroke length of the assembly.

* * * * *

UNITED STATES PATENT AND TRADEMARK OFFICE
CERTIFICATE OF CORRECTION

PATENT NO. : 5,263,934
DATED : 23 November 1993
INVENTOR(S) : Abraham van den HAAK It is certified that error appears in the above-indentified patent and that said Letters Patent is hereby corrected as shown below:

| Column | Line | |
|---|---|---|
| 2 | 67 | Change "inwardly..resilient" to --inwardly resilient--. |
| 5 | 49 | After "liquid" insert --,--; change "the, end" to --the end--. |
| 8 | 51 | Change "stoke" to --stroke--. |
| 10 | 26 | After "assembly" insert --,--. |
| 10 | 38 | After "drawing" change "an" to --in--. |
| 10 | 61 | After "length" insert --of the--. |

Signed and Sealed this

Second Day of August, 1994

Attest:

BRUCE LEHMAN

*Attesting Officer*     Commissioner of Patents and Trademarks